United States Patent [19]

Herrick

[11] Patent Number: 5,163,959
[45] Date of Patent: Nov. 17, 1992

[54] METHOD FOR TREATING AN EYE WITH A CANALICULAR IMPLANT HAVING A COLLAPSIBLE FLARED SECTION

[76] Inventor: Robert S. Herrick, 4134 N. Rosemead Blvd., Rosemead, Calif. 91770

[21] Appl. No.: 830,374

[22] Filed: Jan. 31, 1992

Related U.S. Application Data

[62] Division of Ser. No. 502,437, Mar. 29, 1990.

[51] Int. Cl.$^5$ .............................................. A61F 2/02
[52] U.S. Cl. ..................................... 623/11; 128/887; 128/898; 604/294
[58] Field of Search ................... 623/4, 11, 12; 604/9, 604/104, 264, 285, 294; 128/831, 833, 834, 839, 843, 887, 898

[56] References Cited

U.S. PATENT DOCUMENTS

| | | | |
|---|---|---|---|
| 3,683,904 | 8/1972 | Forster | 128/834 |
| 3,949,750 | 4/1976 | Freeman | 128/260 |
| 4,461,295 | 7/1984 | Herrick | 128/303.1 |
| 4,650,851 | 3/1987 | Rhum et al. | 606/231 |
| 4,660,546 | 4/1987 | Herrick et al. | 604/274 |

OTHER PUBLICATIONS

"The Punctum Plug: Evaluation of a New Treatment for Dry Eye"; Freeman; Amer. Acad. of Ophth. and Optometry; PP. OP-874-OP879, vol. 79, Nov.-Dec. 1975.
"Diagnosis and Treatment of Keratoconjunctivitis"; New Orleans; Barraquer et al., Acad. of Ophthalmology, 1980, p. 43.
"Intra-Canalicular Gelatin Implants in the Treatment of Kerato-Conjunctivitis Sicca"; Wallace S. Foulds; Brit. J. Ophthal. (1961) vol. 45, pp. 625-627.
"Blinking and the Mechanics of the Lacrimal Drainage System"; Marshall G. Doane; Ophtholmology, vol. 88, No. 8, Aug. 1981, pp. 844-851.
"Lacrimal Function", L. T. Jones et al.; American Journal of Ophthalmology 73; 1972, pp. 658-659.

*Primary Examiner*—Randy C. Shay
*Attorney, Agent, or Firm*—Daniel J. Meaney, Jr.

[57] ABSTRACT

A method for treating an external eye condition due to a deficiency of tears as shown. The method includes the steps of testing the eye to determine if a tear deficiency exists. If a tear deficiency is determined to exist, the method includes the step of placing a removable implant being formed of a dimension to pass through the punctum opening and canaliculus of an eye and having an elongated central member including a central axis and a pair of ends wherein one end of said pair of ends has a collapsible flared section having a substantially uniform shape therearound and including means for enabling said collapsible flared section to be uniformly collapsed relative to the central axis in response to the application of force on the collapsible flared section in a direction to collapse the same and urge the collapsible flared section into a collapsed position into and past the punctum opening and into a selected location within the canaliculus causing the collapsible flared section to be collapsed within and to occlude the canaliculus.

15 Claims, 3 Drawing Sheets

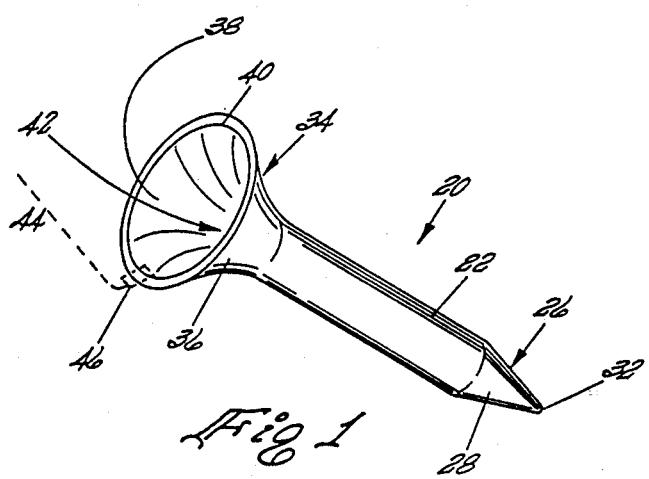
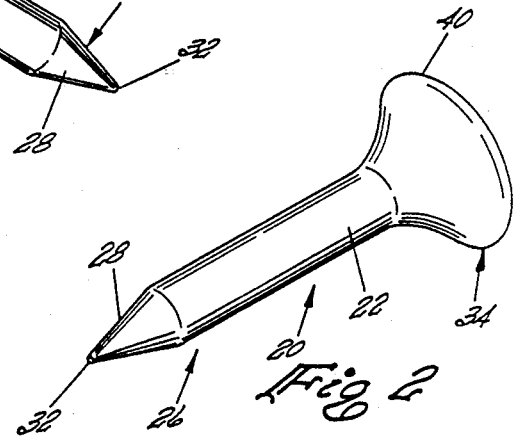
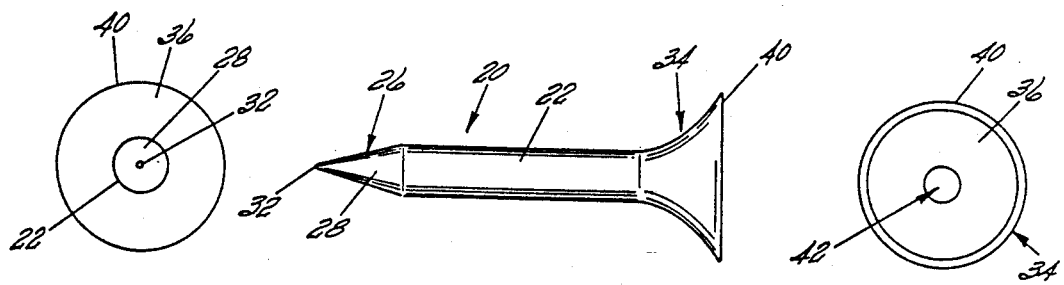
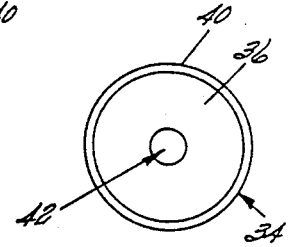

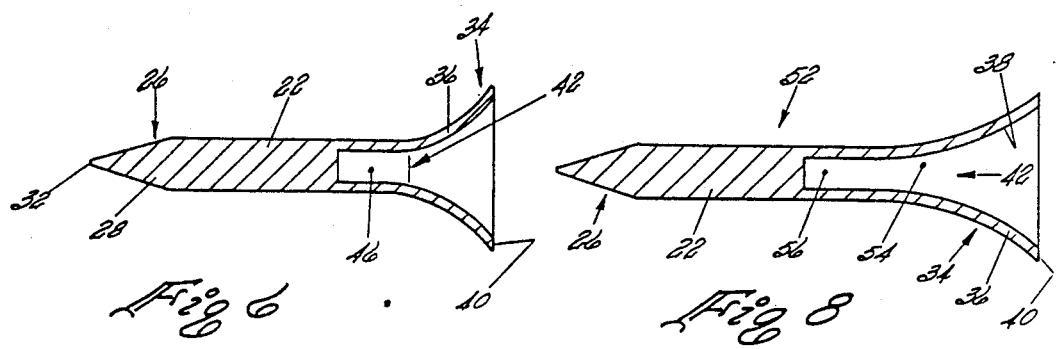
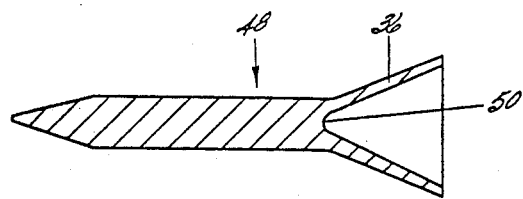
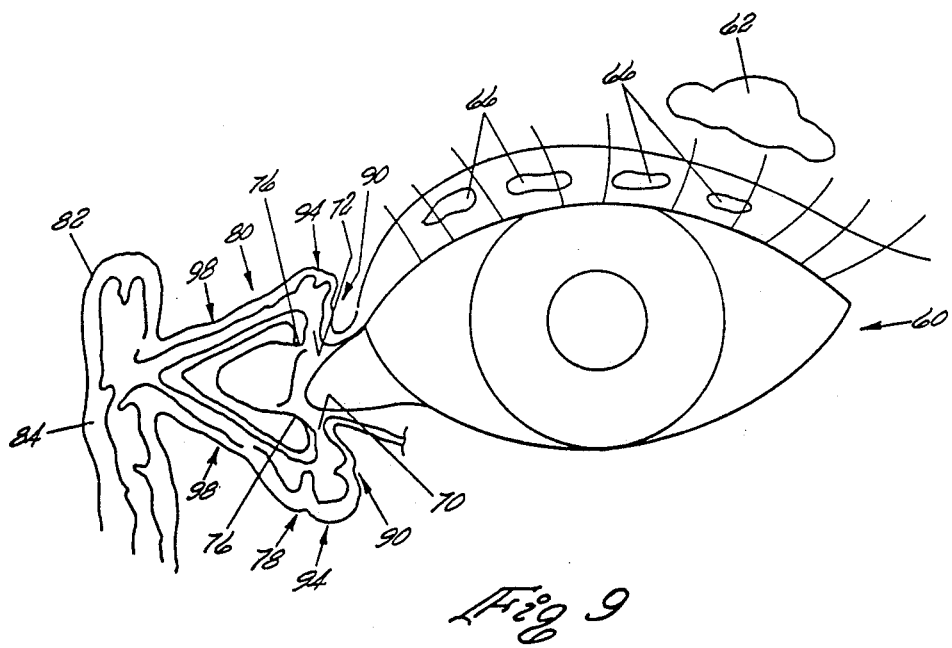

METHOD FOR TREATING AN EYE WITH A CANALICULAR IMPLANT HAVING A COLLAPSIBLE FLARED SECTION

This is a division of application Ser. No. 07/502,437 filed Mar. 29, 1990 now abandoned.

A canalicular implant adapted to be inserted into the punctum of an eye and which is adapted to be transported into the horizontal portion of the canaliculus to occlude the same is shown. The implant comprises an elongated member having a medial end, an opposed lateral end and a central member having a predetermined dimensional cross-section extending therebetween. The medial end has a tapered section which slopes and decreases in cross-section as it extends towards the medial end. The tapered section terminates in a medial tip having a dimension which enables the medial tip to enter and pass through the punctum. The lateral end has a collapsible flared section which increases in cross section as it approaches the lateral end and which terminates in an outer edge having dimension which is greater than the predetermined dimensional cross section of the central member. The collapsible flared section has a fully extended position and a collapsed position. The dimension of the collapsible flared section is approximately equal to the geometrical dimension of the horizontal section of a canaliculus of an eye adapted to receive the same. A radial force applied in a direction to collapse the outer edge of the collapsible flared section urges the same from its fully extended position into the collapsed position.

A method for treating external eye condition due to a deficiency of tears utilizing the canalicular implant is also shown.

BACKGROUND OF THE INVENTION

1. Field of the Invention

This invention relates to a canalicular implant adapted to be utilized in the treatment of a human eye having a deficiency of tears and more specifically relates to a canalicular implant having means defining a tapered section at one end thereof which slopes in the direction towards the first end and means defining a collapsed flared section at a second end thereof.

This invention also relates to a method for treating external eye conditions due to a deficiency of tears utilizing the canalicular implant having a collapsible flared section at one end thereof.

2. Description of the Prior Art

It is known in the art that certain eye problems are related to the volume of tears on the surface of the eyes. Certain of these problems include dry eyes, corneal ulcer, conjunctivitis, blepharitis, contact lens problems and many other external eye diseases.

One method for treating for a deficiency of tears is disclosed in U.S. Pat. No. 4,660,546, wherein the inventor is the same inventor of the present invention. U.S. Pat. No. 4,660,546 discloses a method for treating external human eye conditions due to a deficiency of tears which includes the step of temporarily blockading the canaliculus of the patient and observing over a preselected period of time the response of the patient's eye to the temporary blockage and to determine if any improvement in the eye condition has been achieved in response to the occlusion. If an improvement in eye condition is noted, an implant is placed within the horizontal portion of at least one of the canaliculi of the patient. A temporary blockading of the canaliculus is performed by placing a dissolvable, removable element, which may be in the form of a collagen material or other dissolvable material such as, for example, catgut, in the canaliculus. Unless removed shortly after insertion, the dissolvable implant is absorbed by the body in approximately a two week period. A determination is first made if the canaliculus blockage results in an improvement in the eye condition or other conditions caused by related nasal congestion warranting permanent blockage of the canaliculus, for example, the patient will respond to a partial 60% to 80% retention of constant tears. If permanent blockage of the canaliculus is warranted, U.S. Pat. No. 4,660,546 discloses that the permanent blocking of the canaliculus is performed by utilizing a permanent implant. U.S. Pat. No. 4,660,546 discloses that the permanent implant is fabricated of a nonabsorbable or non-dissolvable material and is in the form of a cylindrically shaped central body having a tapered end or an end of reduced diameter to facilitate the implantation of the implant into and for removal of the implant from the canaliculus. Both the temporary collagen implant or other dissolvable material and the permanent implant disclosed in U.S. Pat. No. 4,660,546 are in the form of a cylindrically shaped central member having a predetermined diameter which may terminate at one end in a tapered end and which reduces in diameter as it slopes away from the central member to form a tapered tip to facilitate insertion of the implant through the punctum, throught vertical canaliculus and into the horizontal portion of the canaliculus.

U.S. Pat. No. 4,461,295, wherein the inventor thereof is the same as the inventor of the present invention, discloses another treatment method which is a method for lasar punctal occlusion. It is known in the art that punctal occlusion has been proven to be an effective way of treating patients which conditions such as sinusitis, hay fever, middle eye infection (chronic), post nasal drip, front headache and other such conditions. The treatment method disclosed by U.S. Pat. No. 4,461,295 includes the use of a temporary suture to stitch the tear drainage canals of the eyes closed to determine if a greater tear volume on the surface of the eyes would improve certain eye problems. This diagnostic procedure has become known in the art as the Herrick Stitch Test. The Herrick Stitch Test is performed by anesthetizing the local area around the lower or upper punctum of the eye. A stitch is carefully placed to occlude the punctum by an eye surgeon utilizing magnification of the eye. After a preselected period of time using the Herrick Stitch Test, the eye surgeon determines if the eye condition has improved, if so, then the eye surgeon permanently closes the punctum by using an ARGON lasar. The punctum may be reopened at a later time if excess tearing is experienced. The reopening of the punctum can be performed by surgical and lasar techniques, all as disclosed in U.S. Pat. No. 4,461,295.

It is also known in the art to utilize other plugs and or techniques for occluding the punctum. One plug device which is known in the art is referred to as a punctum plug which is described in an article by Jerre M. Freeman, M.D., entitled "The Punctum Plug: Evaluation of a New Treatment for the Dry Eye" which appeared in the publication of the transcripts of the Americal Academy of Ophthalomology and Optometry, pages OP-874 through OP-879 (hereinafter referred to as the "Freeman Reference"). In addition, the same punctum plug is disclosed and described in U.S. Pat. No. 3,949,750.

The punctum plug disclosed in the Freeman Reference and in U.S. Pat. No. 3,949,750 is a plug which is adapted to be inserted into the upper and/or lower punctal openings of the eye to block or occlude the punctum. The punctum plug of Freeman is a rod-like plug formed with an oversized tip or barb portion that dialates and blockingly projects into the vertical canaliculus. The punctum plug has a smaller neck or waist portion around which the punctum sphincter ring tightens. The punctum plug has relatively large, smooth head portion which rests on top of the punctal opening and prevents the plug from passing down into the canaliculus. The smooth head portion is designed to be domed shaped to permit the head to rest in the lacrimal lake and against the conjunctiva and cornea with little irritation. The head portion functions to prevent the punctum plug from passing into the horizontal portion of the canaliculus. The punctum plug of Freeman is subject to being inadvertantly removed from the eye by the patient.

It is also known in the art to provide for a temporary closure of the punctum by heat using a light cautery around and in the punctal opening. The punctal closure procedure is disclosed in an article entitled "Diagnosis and Treatment of Keratoconjunctivitis Sicca" which appeared in a symposium on medical and surgical diseases of the cornea, transactions of the New Orleans Academy of Opththalmology in 1980 at page 43 wherein the authors thereof were Jose I. Barraquer, M.D. and eight other authors (hereinafter referred to as the "Barraquer Reference"). The Barraquer Reference further discloses that other treatment methods of temporarily closing the punctum include use of gelatin plugs, cyanoacrylate adhesives and diathermy. The use of intracanalicular gelatin implants for treatment of eye conditions is described in an article entitled "INTRA-CANALICULER GELATIN IMPLANTS IN THE TREATMENT OF KERATO-CONJUNCTIVITIS SICCA" by Wallace S. Foulds which appeared in the Brit J. Ophthal (1961) in Volume 45 at pages 625 through 627, inclusive, (the "Foulds Reference"). The Foulds Reference discloses that occlusion of the lacrimal puncta can be performed by use of and insertion of a fine, water soluble gelatin rod into the punctal openings. The gelatin rod is formed from pure powdered gelatin to which a small quantity of distilled water has been added and is heated in a water bath until the gelatin dissolves and a thick gel results. By dipping a cold glass rod into the so prepared gelatin, and withdrawing the same, fine solid rods of gelatin were formed. The so formed gelatin rods were then inserted into the canaliculi to provide a temporary blockage. As such, the gelatin rod implants, although very fragile, provide an alternate known means for temporarily blocking the canaliculus. If an improvement in eye condition is obtained, then permanent closure of the canaliculi may be warranted.

It is known in the art that a Schirmer's test can be utilized to measure gross tear secretion. If the results of the Schirmer tear secretion test discloses that an insufficient portion of the tear secretion is retained on the eyes, a temporary or permanent occlusion of the canaliculi may prove helpful to improving the above described external eye conditions.

SUMMARY OF THE PRESENT INVENTION

The present invention discloses a new, novel and unique canalicular implant which comprises an elongated central member having a medial end and a lateral end wherein the medial end has a tapered section which slopes in a direction towards the medial end and wherein the lateral end has a collapsible flared section. In the preferred embodiment of the present invention, the implant is a canalicular implant which is adapted to be inserted into the punctum of an eye and to be transported into the horizontal portion of the canaliculus to occlude the same. The implant includes an elongated member having a medial end and a spaced, opposed lateral end and a central member, having a predetermined cross-sectional dimension, extending from the medial end to the lateral end. The medial end has a tapered section which slopes in cross-section as the tapered section extends towards the medial end and which terminates in a medial tip having dimension which enables the medial tip to enter and pass through the punctum opening. The lateral end has a collapsible flared section which increases in cross-section as the collapsible flared section approaches the lateral end and which terminates in an outer edge having dimension which is greater than the predetermined cross-sectional dimension of the central member. The collapsible flared section has a fully expanded position and a collapsed position wherein the dimension of the collapsed position is approximately equal to the geometrical dimension of the horizontal section of the canaliculus of an eye adapted to receive the same. The application of a radial force to the collapsible flared section in a direction to collapse the outer edge thereof urges the collapsible flared section from its fully extended position into its collapsed position. The canalicular implant may be fabricated from a biodegradable material if it is to be used as a temporary implant, or may be formed of a nonbiodegradable material if it is to be used as a permanent implant.

The known prior art implants for providing temporary and permanent occlusion of the horizontal portion of the canaliculus has certain disadvantages. One disadvantage is that a temporary implant, disclosed by the prior art, may have to be removed before it has been fully dissolved or absorbed, as the case may be. If the eye surgeon is unable to remove any part of or all of the temporary implant, the portion of the temporary implant not removed must remain in the canaliculus until it ultimately is dissolved in the body thereby terminating the occlusion of the canaliculus. Typically, an eye surgeon will utilize the temporary implant as a means for determining if the permanent occlusion of the canaliculi will result in an improvement of eye conditions as described hereinbefore. It is possible for the temporary collagen implant, for example, to migrate from the horizontal portion of the canaliculus and back into the eye or to otherwise not remain in place. Also, the temporary implants ay be too fragile to remove in a single piece during removal thereof, if required, by the eye surgeon.

In addition, the insertion and use of a permanent implant having a central body and a tapered end, which is usually formed of a nonabsorbable or non-dissolvable material, can be utilized to permanently occlude the horizontal portion of the canaliculus. However, such a permanent implant can still migrate within the horizontal portion of the canaliculus. Any migration of a permanent implant is undesirable.

The laser treatment to obtain punctal occlusion, although quite effective, has certain disadvantages. One disadvantage is injection of a local anesthetic is required and the patient may experience some pain or discomfort for one to two days after the procedure. Also, some discharge may occur for seven to ten days. Vision may be blurred for a few days. If the patient wears contact lens, the contact lens may be uncomfortable for a few days.

Therefore, one advantage of the canalicular implant of the present invention is that the implant, when positioned in the horizontal portion of the canaliculus, will be held in place by a clamping force which is developed between the interior walls of the canaliculi against the collapsible flared section of the implant.

Another advantage of the present invention is that the implant includes a collapsible flared section which has an outer edge which is slideably urged against the interior walls of the horizontal section of the canaliculi during insertion and placement to hold the implant in position while concurrently occluding the canaliculi.

Another advantage of the present invention is that the canalicular implant is relatively easy to insert without the necessity of using an injectable anesthetic.

Another advantage of the present invention is that the permanent implant, when positioned in the horizontal portion of the canaliculi, does not cause any tissue irritation or irritation to the eye due to migration of the same out of the canaliculi and through the punctum into the eye.

Another advantage of the present invention is that the canalicular implant is easily removable and does not cause any discomfort, does not cause any pain to the patient, there is no discharge for several days, the patient's vision is not subject to blurring for several days and, if the patient wears contact lens, the contact lens will not be uncomfortable for several days.

Another advantage of the present invention is that due to the clamping action between the collapsible flared section of the lateral end of the implant and the interior walls defining the horizontal portion of the canaliculi, the canalicular implant cannot be easily or readily dislodged by patient activity or movement.

Another advantage of the present invention is that an elongated, thread-like member can be attached to the outer ring of the collapsible flared section and be of sufficient length to extend from the canalicular implant, located within the horizontal portion of the canaliculus, to the punctum such that an eye surgeon can apply a pulling force on the thread-like member to retrograde and remove the canalicular implant.

Another advantage of the present invention is that the canalicular implant causes no long term discomfort to the user when the same is in place.

Another advantage of the present invention is that the canalicular implant is effective in blocking a drainage of tears through the horizontal portion of the canaliculi. Thus, if only a partial blockage of drainage of tears is required, the canalicular implant can be inserted into one of the horizontal portions of the upper and lower canaliculus. If full blockage of both canaliculi are required to obtained maximum blockage of the drainage of tears, a canalicular implant can be inserted into each of the horizontal sections of the upper and lower canaliculus.

Another advantage of the present invention is the collapsible flared section of the canalicular implant can include a hollowed out central area which defines a thin walled, conical-shaped flared section.

Another advantage of the present invention is that the thin walled, conical-shaped flared section can terminate in an outer edge.

Another advantage of the present invention si that the collapsible flared section of the canalicular implant can include a "V" shaped central section which is adapted to cooperate with an insertion tool.

Another advantage of the present invention is that the collapsible flared section of the canalicular implant can include a central opening or an elongated central opening which is adapted to cooperate with an insertion tool.

Another advantage of the present invention is that the cross-section diameter of the central member preferably would have a diameter of about 0.2 mil to about 1.2 mil while the outer edge of the collapsible flared section can have a diameter in the order of about 0.5 mil to about 1.5 mil.

Another advantage of the present invention is that the canalicular implant can be formed of a nonabsorbable or non-dissolvable material such as silicone, polytetrafluoroethylene (e.g. Teflon) or other medically compatible non-biodegradable material.

Another advantage of the present invention is that the canalicular implant could be formed of an absorbable or dissolvable material to function as a temporary implant. One such absorbable or dissolvable material that could be utilized for practicing this invention is collagen.

BRIEF DESCRIPTION OF THE DRAWINGS

The foregoing and other advantages of this invention will be apparent from the following description of the preferred embodiment of the invention when considered with the illustrations and accompanying drawings which include the following Figures:

FIG. 1 is a front perspective view of a canalicular implant having a tapered section at the medial end and a collapsible flared section at the lateral end showing the top, front and right end of the preferred embodiment;

FIG. 2 is a bottom perspective view of the canalicular implant of FIG. 1 showing the bottom, rear and left end of the preferred embodiment;

FIG. 3 is a front elevational view thereof;

FIG. 4 is a right side elevational view thereof;

FIG. 5 is a left side elevational view thereof;

FIG. 6 is a cross-sectional view of the canalicular implant of FIG. 1, having central opening in the center of the collapsible flared section which is adapted to cooperate with an insertion tool;

FIG. 7 is a cross-sectional view of an alternate embodiment of a canalicular implant having a "V" shaped central section which is adapted to cooperate with an insertion tool;

FIG. 8 is a cross-sectional view of yet another embodiment of a canalicular implant having an elongated central opening which is adapted to cooperate with an insertion tool;

FIG. 9 is a pictorial representation of a lacrimal system of the eye having an upper and lower canaliculus, each of which have a vertical portion, an ampula or sac and a horizontal portion;

FIG. 10 (b) illustrates the canalicular implant passing through the vertical section of the canaliculus; FIG. 10 (c) illustrates the canalicular implant being positioned past the ampula or sac and entering the horizontal section of the canaliculus; and FIG. 10 (d) illustrates the canalicular implant positioned within and occluding the horizontal section of the canaliculus.

DESCRIPTION OF THE PREFERRED EMBODIMENT

Figure 10A:
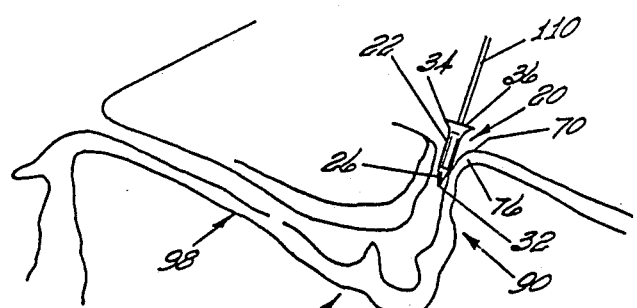
FIGS. 10 (a) through 10 (d) are pictorial representations of the steps of insertion of a canalicular implant of the present invention into the canaliculus wherein FIG. 10 (a) illustrates the canalicular implant being passed through the punctal opening.
Figure 10B:
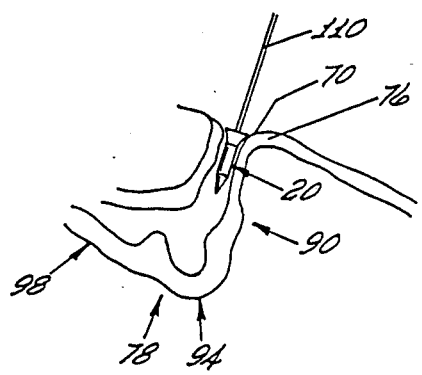
Figure 10C:
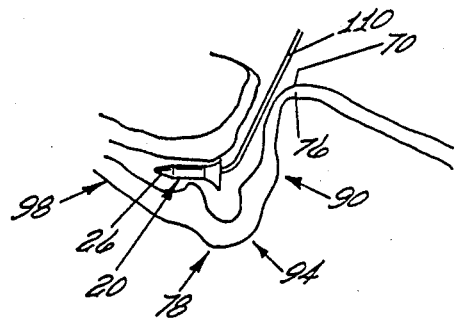
Figure 10D:
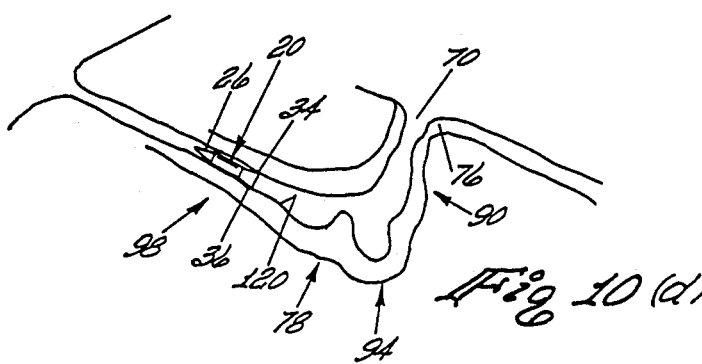

As illustrated in FIG. 1, the canalicular implant is shown generally as 20 and includes an elongated central member 22 which defines a central member of the canalicular implant 20. The canalicular implant includes an elongated central member 22 having a pair of ends 26 and 34 wherein one of the pair of ends includes means defining a collapsible flared end 36. In the preferred embodiment, the elongated central member 22 has a first end or medial end 26 which has a tapered section 28 which slopes in a direction towards the medial end 26 to define a medial tip 32 at the medial end thereof. The elongated central member 22 has a second end or lateral end 34 which has the collapsible flared section 36. In the preferred embodiment, the collapsible flared section 36 forms hollowed out central area defining a thin-walled, conical-shaped member 38 having an outer ring 40 which can be characterized as having the shape of a trumpet. The thin-walled, conical-shaped member 38 of the collapsible flared section 36 has thin walls which are inwardly sloping towards a central section 42. The central section 42 is adapted to cooperate with an insertion tool to facilitate the insertion of the canalicular implant through the punctum and through the canaliculus as described in connection with FIGS. 10 (a) through 10 (d) hereinbelow.

In the preferred embodiment, the central opening extends inwardly into the central member 22 and preferably has a cross-section as illustrated in FIG. 6 thereof. However, the central section 42 could be in the form of a "V" which is likewise adapted to cooperate with an insertion too. This embodiment is illustrated in greater detail in FIG. 7 hereof.

FIG. 1 also shows that a thread-like member shown by dashed line 44 is attached to the outer ring 40 at attachment point shown by dashed area 46. The thread-like member 44 extends through the canaliculus and the punctal opening to the exterior of the punctal opening. The thread-like member 44 provides a means for the eye surgeon to remove the canalicular implant 20 after the same is inserted into the canaliculus. When the surgeon desires to retrograde, remove or withdraw the canalicular implant from the canaliculus, a pulling force can be applied by the eye surgeon to the thread-like member 44 which transmits the pulling force to the outer edge 40 of the collapsible flared end 36. By applying a sufficient pulling force to the thread-like member 44, the surgeon can withdraw the entire canalicular implant from the horizontal portion of the canaliculus and pass the same through the punctal opening of the eye thereby removing the same.

The thread-like member 44 can have a cross-sectional dimension in the order of about 0.2 mm to about 0.5 mm with a dimension of about 0.25 mm being preferred. The length of the thread-like member 44 can be in the order of 10 mils to about 15 mils with a length of about 12 mils being preferred.

FIGS. 2, 3, 4 and 5 show the relationship between the central member 22, the medial end 26 and the lateral end 34 having the collapsible flared section 36. The slope of the medial end 26 which terminates in the medial tip 32 is, in the preferred embodiment, in the order of about 5° to about 15° with a slope of about 8° being preferred. The slope is selected to have a dimension so as to gently and equally expand the sphincter muscle surrounding the punctal opening to uniformly dialate the same to facilitate the insertion of the medial tip 32 and the central member 22 into and through the punctum so as to permit the canalicular implant to be transported into the canaliculus as described in greater detail in FIGS. 10 (a) through 10 (d) hereof.

The cross-sectional view of FIG. 6 shows in greater detail the structure of the canalicular implant of FIG. 1. The central member 42, which is located in the interior portion of the thin walled conical-shaped member 38, has a central opening 46 which extends centrally into the central member 22. In FIG. 6, the depth of the central opening is selected to hold the distal end of the insertion tool to apply a downward or insertion force along the axis of the central member 22 towards the medial end 26.

FIG. 7 illustrates an alternate embodiment of a canalicular implant shown generally as 48 which includes the collapsible flared section 36 having the thin-walled, conical-shaped member 38. The thin-walled, conical-shaped member 38 small end terminates in a "V" shaped central section 50 which is adapted to cooperate with the tip of an insertion tool.

The cross-sectional dimension and length of the canalicular implant generally determines whether the central section of the thin-walled, conical-shaped member 38 has a central opening, such as such opening 46, illustrated in FIG. 6, or a "V" shaped central section 50 of FIG. 7. For example, the canalicular implant may be of sufficient size to be utilized in the eye of an adult. Therefore, the cross-sectional diameter of the elongated central member 22 may be of sufficient length to accommodate the central opening 42 being formed therein as shown in FIG. 6 or FIG. 8. On the other hand, the canalicular implant could be fabricated for pediatric use (e.g. for use in the eye of a child) such that the length and cross-sectional dimension thereof is substantially smaller than the adult canalicular implant. In such event, the embodiment of a canalicular implant as shown in FIG. 7 may be formed of a "V" shaped central member 50 defining a pediatric canalicular implant such that the tip of an insertion tool can cooperate with the "V" shaped central section 50 to apply an insertion force along the axis of the central body 22 of the canalicular implant 48.

FIG. 8 illustrates yet another embodiment of an canalicular implant 52 having an elongated central member 22, a medial end 26 and a lateral end 34 which terminates in a collapsible flared section 26. In the embodiment of FIG. 8, the cross-sectional dimension and axial length of the elongated central member 22 can be such that the thin-walled, conical-shaped member 38 of the collapsible flared section 36 terminates in an elongated central opening 54 having an extended depth to provide a cavity section 56 which functions as an elongated central opening. The elongated central opening or cavity section 56 is adapted to capture and support a greater portion of the distal end of an insertion tool relative to the embodiments illustrated in FIGS. 6 and 7.

It is envisioned that the embodiments of FIGS. 7 and 8 could likewise have a thread-like member attached thereto in a manner similar to the thread-like member 44, illustrated in FIG. 1, which thread-like member 44 is attached to the outer ring 40 of the thin-walled, conical-shaped member 38 of the collapsible flared section 36.

In order to better understand the teachings of the present invention, and the structure of the eye in its relationship to the present invention, the following brief description of the human eye and the associated lacrimal system illustrated in FIG. 9 and showing the paths of the tears from sources of the tears to the nasal cavity, will first be discussed.

The eye 60 includes a cornea and a pupil which is well known in the art. The source of the tears for the eye 60 is generally classified into "crying tears" and "constant tears". The "crying tears" are produced by a large lacrimal gland 62 illustrated in the upper right hand portion of the illustration of eye 60. The "constant tears" are produced by a series of small glands 66 which are located below the large gland 62 and spaced apart above the cornea of the eye 60. The "constant tears" are the tear secretions which are to be preserved in accordance with the teachings of the present invention.

In the normal eye, approximately 400 drops (9.5 milliliters of tear secretion are produced during the day and a lesser volume of tear secretion is produced at night during sleep. Tear secretion also protects the eye from infection since the tears contain an enzyme called Lysozyme that functions as an antibiotic. With age, the eye produces less tear secretion, about sixty percent (60%) less at age 65 than at age 18. The tears flow over the eyes and drain through the small openings called the puncta or punctal openings. There are two punctal openings in the eye, a lower punctum 70 and an upper punctum 72. The punctal openings 70 and 72 form openings into the corresponding a lower canaliculus 78 and an upper canaliculus 80. Each of the punctal openings 70 and 72 have the sphincter muscle, illustrated as muscle 76, formed therearound. The sphincter muscle 76 is a fairly dense relatively a vascular connective ring of tissue. The lower canaliculus 78 and the upper canaliculus 80 are connected to a lacrimal sac 82. The lacrimal sac 82 is connected to a nasal lacrimal duct 84. The lacrimal duct 84, in turn, extends into the nasal cavity (not shown). The tears produced by the eye travel through the punctal openings, through their associated canaliculus.

As the tears exit the lower canaliculus 78 and the upper canaliculus 80, the tear flows merge in the lacrimal duct 84 and then travel to the nasal cavity. Lower canaliculus 78 and the upper canaliculus 80, which comprise the drainage channels of the eye for tears, are about 10 mm in length. Each of the canaliculi 78 and 80 include a vertically extending portion, shown generally as 90, which have an overall length of approximately 2.5 mm to about 3.5 mm. The vertical portion of the canaliculus 90 is connected to an ampula or sac, shown generally as 94, which has a dimension of about 2 mm to 3 mm at its widest portion. The ampula or sac 94 narrows into the horizontal portion of the canaliculus, shown generally as 98. The horizontal portion of the canaliculus, sometimes referred to as the horizontal canaliculus, has a diameter in the order of about 0.5 mm and an overall length of about 8 mm. In practicing the present invention, the canalicular implant is placed in the horizontal portion 98 of the canaliculus 78 and 80.

It has developed that mechanism of lacrimal drainage results in the drainage of tear flow from the eye. One article which describes this phenomenon is entitled "BLINKING AND THE MECHANICS OF THE LACRIMAL DRAINAGE SYSTEM" by Marshall G. Doane, Ph.D, which appeared in OPHTHALMOLOGY, Volume 88, No. 8, August, 1981, pages 844 through 851 inclusive (the "Doane Article"). The doane Article describes that during each blink cycle, the upper lid sweeps down over the eye. As the lid descends, the pappillae containing the punctal opening elevate from the medial lid margin. As the lid continues to descend, the puncta are occluded by the contact of the lid margins. Further lid closure squeezes the canaliculi and sac forcing the tear or contained fluid to drain into the nasolacrimal duct. At the end of a complete lid closure, the lacrimal system is compressed and largely empty of fluid. During the opening phase, the puncta are still occluded. The walls of the passageways or canaliculus expand by elastic force causing a partial vacuum or suction. As the lid continues to open, the puncta "pop" apart, excess tear fluid is immediately drawn off the eye and into the canaliculus.

The insertion of an implant into the horizontal portion of the canaliculus tends to retard the squeezing action of the canaliculi during eyelid closure and to reduce the partial vacuum during eyelid opening which results in a larger quantity of tear fluid remaining on the eye. If medication is added to the eye, it remains on the eye longer thereby effecting the eye treatment by the medication which, otherwise, would be removed by the blinking and the mechanics of the lacrimal drainage system.

In utilizing the canalicular implant for practicing the teaching of the invention, the eye surgeon can utilize any one of a number of methods for determining if an external condition due to a deficiency of tears exists. In the preferred embodiment of the present invention, the canaliculus can be temporarily occluded by placing a temporary implant (which may be a temporary canalicular implant) within the horizontal portion of the canaliculus to provide a temporary blockage thereof. By utilizing a temporary implant for providing temporary blockage of the canaliculus, the eye surgeon can observe the response of the patient to the temporary blockage. If an improvement in the eye condition of the patient is noted, a permanent canalicular implant can be implanted within the horizontal section of the canaliculus in at least one of the canaliculi of the patient.

It is envisioned that the temporary implant used in practicing the invention can be in the form of one of the embodiments described hereinbefore with respect to FIGS. 1 through 8 of the present invention. If a canalicular implant is to function as a temporary canalicular implant to provide temporary blockage of the canaliculus, the temporary canalicular implant can be fabricated from a medically acceptable, dissolvable biodegradable material such as collagen, catgut, biodegradable suturing material, polyglen acid or the like. The temporary canalicular implant can be inserted into the horizontal portion of the canaliculus utilizing the procedures set forth hereinbelow in FIGS. 10 (a) through 10 (d).

If the eye surgeon determines that a permanent occlusion of the canaliculus is desirable, a permanent canalicular implant can be utilized as a means for providing a permanent occlusion of the horizontal section of the canaliculus. In such event, the permanent canalicular implant can be fabricated from a non-biodegradable material or material and one which is not absorbable by or dissolved in the human body. Examples of such materials are medical grade rubber, silicone, polyethylene, polypropylene, polytetrafluoroethylene (e.g. Teflon) are some of the materials. The diameter of the canalicular implant would be in the order of about 0.2 mm to about 1.2 mm and the overall length could be in the order of about 4 mm to about 8 mm. The preferred diameter for the canalicular implant is in the order of about 0.5 mm. The thickness of the thin-walled, conical shaped member may be in the order of about 700 mm in the preferred embodiment.

Referring now to the pictorial representations of FIGS. 10 (a) through 10 (d). FIGS. 10 (a) through 10 (d) illustrate the method for inserting the canalicular implant into the canaliculus of the eye. In FIGS. 10 (a) through 10 (d), the pictorial representations are shown based upon the canalicular implant 20 be inserted into the horizontal section of the lower canaliculus 78. Of course, the canalicular implant could be inserted into the upper canaliculus 80 in a similar manner as described below. As illustrated in FIG. 10 (a), an insertion tool 110 is inserted into the collapsible flared section 36 of the implant and cooperates with the central section thereof such that the distal end or tip of the insertion tool 110 is contiguous the central section defined by the thin-walled, conical-shaped member 36 of the collapsible flared section 38. The canalicular implant 20 is positioned with the medial tip 32 of the medial end 26 penetrating the punctal opening 70 such that the medial tip 32 will gently expand the sphincter muscle 76 defining the punctal opening 70. The central body 22 is then passed through the punctal opening 70 until the punctal opening engages the exterior surface of the collapsible flared section 36.

FIG. 10 (b) illustrates teat the sphincter muscle 76 slightly engages the collapsible flared section 36 as an insertion force is applied to the canalicular implant 20 by the insertion tool 110. A radial force is applied around the surface of the collapsible flared section 36 as the canalicular implant 20 slideably moves past the sphincter muscle 76. The sphincter muscle 76 applies a radial force to the collapsible flared section 36 in a direction so as to cause the collapsible flared section to be urged into its collapsed position.

FIG. 10 (c) illustrates that the insertion tool 110 continually applies an insertion force transporting the canalicular implant 20 through the vertical portion of the canaliculus 90 and into the ampula or sac 94. Due to the increased diameter of the ampula or sac, the insertion tool 110 is utilized to turn the medial end 26 of the canalicular implant 20 towards and into the horizontal portion of the canaliculus 98. FIG. 10 (c) illustrates the position of the canalicular implant 20 after it has been transported through the ampula or sac 94 and as it is just entering into the horizontal portion of the canaliculus 98.

FIG. 10 (d) illustrates the canalicular implant 20 positioned within and occluding the horizontal portion of the canaliculus 98. The collapsible flared section 36 slideably engages the interior walls 120 of the horizontal section of the canaliculus 98. A clamping pressure is developed by the interior walls 120 against the outer ring 40 of the conical-shaped member 38 of the collapsible flared section 36 which holds the canalicular implant 20 in place by virtue of the clamping force developed between the collapsible flared section 36 and the interior walls 120 defining the horizontal portion of the canaliculus 98.

Figure 11:
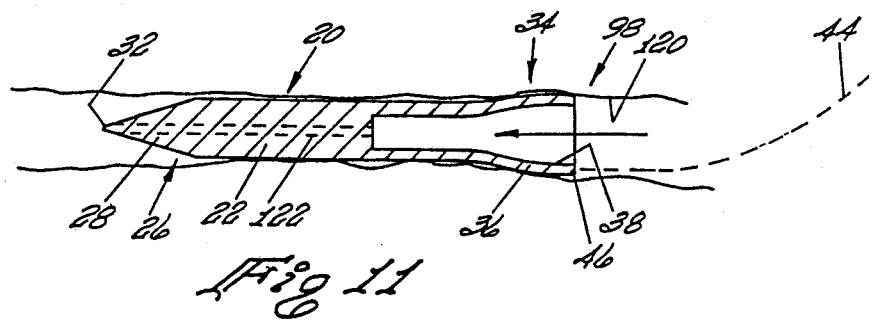
FIG. 11 is an enlarged pictorial representation showing the collapsible flared section of the canalicular implant in its collapsed position when the same is positioned within and occludes the horizontal section of the canaliculus.

FIG. 11 illustrates pictorially the collapsible flared section 36 of the canalicular implant 20 in its collapsed position and illustrates that the central member 22 intimately engages the interior walls 120 of the horizontal portion of the canaliculus 98. Due to the clamping force developed between the collapsible flared section 38 and the interior walls 120, the canalicular implant is held firmly in place and will not migrate or retrograde within the horizontal portion of the canaliculus 98. However, the canalicular implant can be removed by applying a pulling force on the thread-like member 44 as described above relative to FIG. 1.

By utilizing the teachings of the present invention, a method for treating external eye conditions due to a deficiency of tears is disclosed. The method includes the steps of testing the eye to determine if a tear deficiency exists; and, if a tear deficiency is determined, placing a canalicular implant having an elongated central member, a first end and a second end wherein the first end has a tapered section which slopes towards the first end and a second end having a collapsible flared section, within the horizontal portion of at least one of the canaliculi.

The present invention also teaches a method for surgically inserting an implant through a punctum opening into the horizontal of at least one of the canaliculi having interior side walls of an eye for treating external eye condition due to a deficiency of tears. The method comprises the steps of inserting an implant having an elongated central member and a first end and a second end wherein the first end has a tapered towards the first end terminating in a tip and the second end has a collapsible flared section which has a fully extended position and a collapsible position wherein the tip thereof is passed through the punctum opening of the at least one of the canaliculi with the collapsed flared section in its fully extended position; and urging the tip of the implant into the horizontal section of the at least one canaliculi to transport the collapsed flared section into the horizontal section of the at least one canaliculi which slideable engaged the interior side walls of the at least one canaliculi to apply a radial force against the collapsible flared section urging the same into its collapsed position to occlude the horizontal section of the at least one canaliculi.

The step of urging in the above described method can include using a tool which is inserted into the collapsible flared section to apply force to urge the implant through the punctum opening and ultimately into the horizontal section of at least one of the canaliculi.

The canalicular implant of the present invention utilizes the collapsible flared section as a means for both occluding the horizontal portion of a canaliculi, in which it is inserted, and concurrently develops a clamping force between the collapsible flared section and the interior walls of the canaliculi to hold the canalicular implant in place. The collapsible flared section is located, in the preferred embodiment, at one end of the elongated central member. Preferably, the other end of the elongated central member is tapered. However, it is envisioned that the end of the canalicular implant which is located opposite to the end thereof which includes means defining the collapsible flared section can be formed with any one of a plurality of ends. Examples of such ends could be a wedge-shaped end, a spherical-shaped end or other shape which would perform the function of gently expanding the sphincter muscle as the canalicular implant penetrates the punctum opening to transport the canalicular implant through the punctal opening and into the horizontal section of the canaliculus.

The canalicular implant of the present invention is preferably used as a permanent implant for practicing the invention. In the method disclosed and taught herein, the temporary implant could be an implant well known in the art, could be a means for occluding the punctal opening, could be a temporary implant as disclosed in the prior art section above or any other means known in the art for temporarily occluding the eye to determine if an improvement in eye condition is noted.

However, the temporary implant could, likewise, be a canalicular implant having a structure disclosed herein wherein the implant is formed of an absorbable or dissolvable (in the body) biodegradable material. The permanent canalicular implant can be identical in shape, size and dimension but be formed of a non-biodegradable, nonabsorbable or non-dissolvable (in the body) material. The advantage of utilizing a temporary implant and a permanent implant which has a structure as disclosed herein is that the collapsible flared section of the canalicular implant performs the function of preventing migration of the implant within the horizontal section of the canaliculus by developing a clamping pressure between the collapsible flared section and the interior walls of the canaliculi while concurrently providing a blockade to the canaliculus.

If it is desirable to have a small passageway available to enable a flow of tears to pass through the occlusion, it is envisioned that the canalicular implant could have an aperture extending axially through the center thereof, for example an extended opening shown by dashed opening 122 in FIG. 11, to provide a passageway of a predetermined diameter to control tear secretion flow or, the alternative, a slot could be formed around the periphery thereof to facilitate a partial tear flow.

It is also envisioned that the canalicular implant of the present invention could include material which is responsive to actinic radiation shown by arrow 122 in FIG. 11, such as for example X-rays, so that the eye surgeon can perform tests to determine if the canalicular implant is properly located within the horizontal section of the canaliculi. One such material that can be utilized is barium, in appropriate concentrations known to persons skilled in the art, so as to be responsive to actinic radiation, such as X-rays. The use of such materials responsive to actinic radiation is of such a low enough level that it does not cause any adverse effects to the patient into which a canalicular implant containing the same is implanted.

What is claimed is:

1. A method for treating an external eye condition due to a deficiency of tears including the steps of
    testing the eye to determine if a tear deficiency exists; and
    if a tear deficiency is determined to exist, placing a removable implant into the canaliculus of the eye, the implant being formed of a dimension to pass through the punctum opening and canaliculus of an eye and having an elongated central member including a central axis and a pair of ends wherein one end of said pair of ends has a collapsible flared section having a substantially uniform shape therearound and including means for enabling said collapsible flared section to be uniformly collapsed relative to the central axis in response to the application of force on the collapsible flared section in a direction to collapse the same and urge the collapsible flared section into a collapsed position, said placing step including inserting the implant through the punctum opening of the eye and into a selected location within the horizontal portion of the canaliculus, thereby causing the collapsible flared section to be collapsed within and to occlude said canaliculus.

2. A method for surgically inserting an implant through a punctum opening into a canaliculus having interior side walls of an eye for treating external eye condition due to a deficiency of tears comprising the steps of
    inserting an implant into the canaliculus of an eye, the implant being formed of a dimension to pass through the punctum opening and canaliculus of the eye and having an elongated central member including a central axis and a first end and a second end wherein the first end has a taper towards the first end terminating in a tip and the second end has a collapsible flared section having a substantially uniform shape therearound and including means for enabling said collapsible flared section to be uniformly collapsed relative to the central axis in response to the application of force on the collapsible flared section in a direction to collapse the same and urge the collapsible flared section from a fully extended position into a collapsed position, wherein the tip of said first end is passed through the punctum opening of the canaliculus with the collapsible flared section in its fully extended position; and
    urging the tip of said first end into the canaliculus to transport the collapsible flared section into a selected location within the canaliculus wherein said collapsible flared section slideably engages the interior side walls thereof whereby said side walls apply a radial force against the collapsible flared section urging the same into its collapsed position to occlude said canaliculus.

3. The method of claim 2 wherein said step of urging includes using a tool which is inserted into the collapsible flared section to apply a force to urge the implant through the punctum opening and into the canaliculus.

4. A method for treating an external eye condition comprising the steps of:
    inserting an implant into the canaliculus of an eye, the implant being formed of a dimension to pass through the punctum opening and canaliculus of an eye and having an elongated central member including a central axis, a first end and a second end, wherein said second end has a collapsible flared section having a substantially uniform shape therearound and including means for enabling said collapsible flared section to be uniformly collapsed relative to the central axis in response to the application of force on the collapsible flared section in a direction to collapse the same and urge the collapsible flared section from a fully extended position into a collapsed position, the inserting step including placing the implant into the punctum opening and into the canaliculus with the collapsible flared section in its fully extended position; and urging the implant through the punctum opening of the eye and into a selected position within the canaliculus thereby causing the collapsible flared section to be collapsed within and to occlude the canaliculus.

5. The method of claim 4 wherein the canaliculus includes a vertical section and wherein the step of urging further includes positioning the implant in the vertical section of the canaliculus.

6. The method of claim 4 wherein the canaliculus includes a horizontal section and wherein the step of urging further includes positioning the implant in the horizontal section of the canaliculus.

7. The method of claim 4 further comprising the step of selecting an implant formed of a biodegradable material to be used in said inserting step.

8. The method of claim 7 further comprising the step of selecting an implant formed of a collagen material to be used in said inserting step.

9. The method of claim 4 further comprising the step of selecting an implant formed of a non-biodegradable material to be used in said inserting step.

10. The method of claim 9 further comprising the step of selecting an implant formed of a silicone material to be used in said inserting step.

11. The method of claim 4 further comprising the step of selecting an implant wherein said first end of the implant is tapered towards the first end and terminates in a tip to be used in said inserting step.

12. The method of claim 11 further comprising the step of urging the tip of said first end into a horizontal section of the canaliculus to transport the collapsible flared section into the horizontal section of the canaliculus wherein the collapsed flared section slideably engages the interior side walls of the canaliculus which apply a radial force against the collapsible flared section urging the same into a collapsed position which will occlude said horizontal section of the canaliculus.

13. The method of claim 12 wherein the step of urging includes using a tool which is inserted into the collapsible flared section to apply force to urge the implant through the punctum opening and into the horizontal section of the canaliculus.

14. The method of claim 4 wherein the canaliculus has interior side walls which define a vertical section and a horizontal section, the urging step further comprising the step of urging the tip of said first end through the punctum opening into the vertical section of the canaliculus and then transporting the collapsible flared section into the horizontal section of the canaliculus wherein said collapsible flared section slideably engages the interior side walls of the canaliculus which apply a radial force against the collapsible flared section urging the same into a collapsed position to occlude said horizontal section of the canaliculus.

15. The method of claim 4 wherein the canaliculus has a vertical section, the urging step further comprising the step of urging the implant sufficiently through the punctum and into the vertical section of the canaliculus causing the collapsible flared section to be collapsed within and to occlude the vertical portion of said canaliculus adjacent the punctum opening.

* * * * *